United States Patent
Couture (10) Patent No.: US 9,173,665 B2
(45) Date of Patent: Nov. 3, 2015

(54) PATIENT-SPECIFIC SURGICAL GUIDE FOR INTRA-OPERATIVE PRODUCTION OF PATIENT-SPECIFIC AUGMENT

(71) Applicant: Zimmer, Inc., Warsaw, IN (US)

(72) Inventor: Pierre Couture, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 306 days.

(21) Appl. No.: 14/019,884

(22) Filed: Sep. 6, 2013

(65) Prior Publication Data

US 2015/0073419 A1 Mar. 12, 2015

(51) Int. Cl.
| | | |
|---|---|---|
| *A61B 17/17* | | (2006.01) |
| *A61F 2/30* | | (2006.01) |
| *A61F 2/40* | | (2006.01) |

(52) U.S. Cl.
CPC ............. *A61B 17/1739* (2013.01); *A61B 17/17* (2013.01); *A61F 2/30942* (2013.01); *A61F 2/4081* (2013.01); *A61B 2017/1778* (2013.01); *A61F 2002/30736* (2013.01)

(58) Field of Classification Search
CPC .... A61B 17/16; A61B 17/17; A61B 17/1703; A61B 17/1707; A61B 17/1739; A61B 2017/1602; A61B 2017/1778; A61F 2/30942; A61F 2002/30736; A61F 2002/3096; B23P 19/10; B23P 15/28; B25B 5/103; B27C 5/08; B27C 5/10
See application file for complete search history.

(56) References Cited

U.S. PATENT DOCUMENTS

| | | | | | |
|---|---|---|---|---|---|
| 5,086,401 | A | * | 2/1992 | Glassman | .......... A61B 19/2203 606/53 |
| 5,112,336 | A | * | 5/1992 | Krevolin | ................ A61B 17/17 606/87 |
| 5,129,907 | A | * | 7/1992 | Heldreth | ............ A61B 17/1677 606/80 |
| 5,129,908 | A | * | 7/1992 | Petersen | ................ A61B 17/16 606/86 R |
| 5,190,547 | A | * | 3/1993 | Barber, Jr. | ............... A61B 17/16 609/79 |
| 5,380,332 | A | * | 1/1995 | Ferrante | ............. A61B 17/1659 606/79 |
| 5,520,692 | A | * | 5/1996 | Ferrante | ............. A61B 17/1677 606/79 |

(Continued)

*Primary Examiner* — Christian Sevilla
*Assistant Examiner* — Eric S Gibson
(74) *Attorney, Agent, or Firm* — Norton Rose Fulbright Canada LLP (57) ABSTRACT

A patient-specific surgical guide for intra-operatively producing a patient-specific augment and a method for producing same are provided. The method includes planning a patient-specific augment using obtained patient imagery of a bone adapted to receive a prosthesis to determine a size and shape of the patient-specific augment corresponding to the bone, creating a model of the patient-specific augment having the determined size and shape, and providing a patient-specific surgical guide having cutting guide surfaces which are customized in position and orientation and configured to guide a surgical implement to form the patient-specific augment corresponding to the 3D model. The patient-specific surgical guide is then used intra-operatively create the augment corresponding to the 3D model.

14 Claims, 6 Drawing Sheets

(56) References Cited

U.S. PATENT DOCUMENTS

| | | | | |
|---|---|---|---|---|
| 5,540,692 A * | 7/1996 | Tidwell | A61B 17/15 | 606/79 |
| 5,616,146 A * | 4/1997 | Murray | A61B 17/1677 | 606/102 |
| 6,159,246 A * | 12/2000 | Mendes | A61B 17/1767 | 606/80 |
| 6,231,577 B1 * | 5/2001 | Canedy | A61B 17/1677 | 409/138 |
| 6,321,457 B1 * | 11/2001 | Lariviere, Jr. | B26B 29/06 | 33/562 |
| 6,488,033 B1 * | 12/2002 | Cerundolo | A61B 17/1637 | 128/898 |
| 7,238,190 B2 * | 7/2007 | Schon | A61B 17/15 | 606/87 |
| 7,344,540 B2 * | 3/2008 | Smucker | A61B 17/158 | 606/87 |
| 7,802,503 B2 * | 9/2010 | Couvillion | B26D 1/08 | 269/87.2 |
| 7,862,570 B2 * | 1/2011 | Russell | A61B 19/26 | 600/424 |
| 7,955,336 B2 * | 6/2011 | Gil | A61F 2/4644 | 606/79 |
| 7,981,158 B2 * | 7/2011 | Fitz | A61B 17/1739 | 128/898 |
| 8,043,315 B2 * | 10/2011 | Shepard | A61B 17/1604 | 606/167 |
| 8,393,266 B2 * | 3/2013 | Rasmussen | B41F 1/02 | 101/287 |
| 8,439,921 B2 * | 5/2013 | Jamali | A61F 17/1635 | 606/79 |
| 8,491,596 B2 * | 7/2013 | Long | A61B 17/1682 | 606/96 |
| 8,545,501 B2 * | 10/2013 | Wong | A61F 2/4644 | 606/79 |
| 8,556,908 B2 * | 10/2013 | Nycz | A61B 17/1764 | 606/87 |
| 8,764,760 B2 * | 7/2014 | Metzger | A61B 17/155 | 606/88 |
| 8,800,158 B1 * | 8/2014 | Shim | A61B 17/1635 | 33/630 |
| 8,945,135 B2 * | 2/2015 | Ries | A61F 2/3877 | 606/86 R |
| 2002/0082604 A1 * | 6/2002 | Abdelgany | A61F 2/4644 | 606/79 |
| 2002/0183760 A1 * | 12/2002 | McGovern | A61B 17/1764 | 606/88 |
| 2003/0236521 A1 * | 12/2003 | Brown | A61B 17/1615 | 606/80 |
| 2004/0034361 A1 * | 2/2004 | Dalton | A61B 17/15 | 606/87 |
| 2004/0097946 A1 * | 5/2004 | Dietzel | A61B 17/15 | 606/79 |
| 2005/0251263 A1 * | 11/2005 | Forrer | A61F 2/4014 | 623/19.13 |
| 2005/0288681 A1 * | 12/2005 | Klotz | A61F 2/4014 | 606/102 |
| 2006/0142872 A1 * | 6/2006 | Klotz | A61F 2/4014 | 623/23.44 |
| 2007/0118141 A1 * | 5/2007 | Marchyn | A61B 17/1677 | 606/88 |
| 2007/0135918 A1 * | 6/2007 | Malinin | A61B 17/1604 | 623/16.11 |
| 2008/0011137 A1 * | 1/2008 | Couvillion | A61B 17/1635 | 83/78 |
| 2009/0240141 A1 * | 9/2009 | Neubauer | A61B 17/1684 | 600/426 |
| 2010/0286710 A1 * | 11/2010 | Boyer | A61B 19/5244 | 606/130 |
| 2011/0130795 A1 * | 6/2011 | Ball | A61B 17/1739 | 606/86 R |
| 2012/0010711 A1 * | 1/2012 | Antonyshyn | A61F 2/2875 | 623/16.11 |
| 2012/0265208 A1 * | 10/2012 | Smith | A61B 17/1626 | 606/87 |
| 2012/0290272 A1 * | 11/2012 | Bryan | A61B 17/1684 | 703/1 |
| 2013/0237991 A1 * | 9/2013 | Iannotti | A61F 2/4603 | 606/102 |
| 2014/0094813 A1 * | 4/2014 | Clever | A61B 17/1767 | 606/88 |
| 2015/0073419 A1 * | 3/2015 | Couture | A61F 2/30942 | 606/87 |
| 2015/0073424 A1 * | 3/2015 | Couture | A61B 17/1739 | 606/96 |
| 2015/0164644 A1 * | 6/2015 | Miquel | A61F 2/30942 | 409/131 |

* cited by examiner

PATIENT-SPECIFIC SURGICAL GUIDE FOR INTRA-OPERATIVE PRODUCTION OF PATIENT-SPECIFIC AUGMENT

CROSS-REFERENCE TO RELATED APPLICATIONS

This is the first filed application for the present invention.

TECHNICAL FIELD

The present disclosure relates generally to orthopedic surgical systems, instruments, tools and prostheses, and more particularly to patient-specific instruments used in orthopedic procedures.

BACKGROUND

During joint arthroplasty procedures, performed to repair a damaged bone of a joint for example, a surgeon may need to remove a quantity of damaged bone in order to prepare it for receiving the orthopedic prosthesis. For example, during a total or partial knee arthroplasty procedure, the surgeon may need to mill the distal femur to provide an attachment surface for receiving a distal femoral prosthesis. Alternately, during a shoulder arthroplasty procedure, the surgeon may need to mill the glenoid region of the scapula, in order to form a suitable attachment surface for receiving a glenoid prosthesis.

With particular reference to orthopedic shoulder arthroplasty, when a surgeon plans the surgery it may become evident that the glenoid is too deformed for an optimum placement with a standard glenoid implant. Certain surgeons more comfortable with such irregularities will plan for an artificial augment or a augment to be used, which is adapted to fit between the implant and the damaged bone to accommodate the deformed glenoid while providing a suitable surface for receiving a standard glenoid implant. However, the planning of such an augment or augment typically needs to be done intra-operatively, once the surgeon is able to see the state of the damaged scapula and thus determine what type and shape of augment or augment may be best suited to accommodate the particular anatomical features. As such, surgeons who perform such surgeries infrequently are less comfortable with performing these additional steps intra-operatively. This is particularly true if a augment is to be used, as it would need to be both planned and created intra-operatively, which can significantly add to the complexity of the surgery. Such surgeons less accustomed to these procedures may, instead, either refer the surgery to another more specialized surgeon or simply decide to place the glenoid implant in a position or orientation that is less than ideal. This can compromise the lifespan of the implant and lead to unwanted complications.

Despite the continuous development of patient-specific instruments and patient-specific implants (hereinafter "PSI"), i.e. instruments and/or implants that are specifically designed and produced to suit the unique anatomical structures of an individual patient (as opposed to generic implants/instruments which are intended for use on all or a large number of different patients), improvements are sought to be able to further personalize orthopedic procedures and systems, particularly with respect to the above-mentioned challenges relating to the intra-operative creation of augments or augments.

SUMMARY

The present invention includes a patient-specific surgical guide and associated system and method for preparing a patient-specific augment or augment adapted to receive an orthopedic prosthesis.

Therefore, in accordance with one aspect of the present disclosure, there is provided a patient-specific surgical guide for intra-operatively creating a patient-specific augment adapted for mounting a prosthetic implant on a bone of a patient, the patient-specific surgical guide comprising: a base fixture including a mounting surface having a bone retaining portion thereon within which an unformed augment blank is receivable; and a patient-specific cutting guide engaged to the base fixture, the patient-specific cutting guide having one or more cutting guide surfaces which are customized in position and orientation for said patient and configured to guide a surgical implement to re-shape the unformed augment blank to create said patient-specific augment, wherein the patient-specific augment has a size and shape corresponding to a portion of the bone adapted to receive the prosthetic implant such that the patient-specific augment will conform to said portion of the bone for abutment therewith; wherein the patient-specific cutting guide is mounted to the base fixture for displacement between an open inoperable position and a closed bone cutting position, the bone retaining portion of the base fixture being accessible to receive the unformed augment blank therein when the patient-specific cutting guide is disposed in the open inoperable position, and the cutting guide surfaces of the patient-specific cutting guide being disposed in position to allow said re-shaping of the unformed augment blank when the patient-specific cutting guide is disposed in said closed bone cutting position.

There is also provided, in accordance with another aspect of the present disclosure, an orthopedic guide for intra-operatively preparing a particular patient's bone to receive a prosthesis, the orthopedic guide comprising: a base fixture including a mounting surface having a bone retaining portion thereon within which an unformed augment blank is receivable; and an interchangeable patient-specific cutting guide removably engaged to the base fixture, the patient-specific cutting guide having one or more cutting guide surfaces which are customized in position and orientation for said patient and configured to guide a cutting tool to re-shape the unformed augment blank on the base fixture into a patient-specific augment, the patient-specific augment including at least one surface thereon having a size and shape corresponding to the particular patient's bone and adapted to fit against the particular patient's bone, such that the patient-specific augment is mountable between the particular patient's bone and the prosthesis.

There is also provided, in accordance with another aspect of the present disclosure, a method of producing a patient-specific augment for use in an orthopedic surgery procedure, the patient-specific augment being adapted for mounting a prosthetic implant on a bone of a patient, comprising the steps of: a) using patient imagery of at least a portion of the bone adapted to receive the prosthetic implant to create a bone model; b) obtaining an implant model of the prosthetic implant; c) planning a preferred position and orientation of the prosthetic implant relative to the bone using the implant model and the bone model; d) determining whether an augment is required to mount the prosthetic implant in said preferred position and orientation on the bone, and planning the patient-specific augment, including using the implant model and the 3D bone model to determine a size and shape of the patient-specific augment such that the patient-specific augment will conform to a surface of said bone for abutment therewith and fit between said surface and the prosthetic implant in said desired position and orientation, and e) creating a three-dimensional model of the planned patient-specific augment; f) providing a patient-specific surgical guide planned and created using the results of step d), the patient-specific surgical guide having cutting guide surfaces which are customized in position and orientation and configured to guide a cutting tool to form the patient-specific augment corresponding to the three-dimensional model thereof; and g) using the patient-specific surgical guide to intra-operatively create the patient-specific augment corresponding to the three-dimensional model.

There is further provided, in accordance with another aspect of the present disclosure, a method for preparing a patient-specific augment adapted for mounting an orthopedic prosthesis to a particular patient's bone, the method comprising the steps of: providing a digital model of the bone; identifying a portion of the bone adapted to receive the prosthesis and determining a preferred position and orientation of the prosthesis relative to said portion of the bone; determining a size and shape of a patient-specific augment having at least one bone-engaging surface corresponding to said portion of the bone, such that the patient-specific augment conforms to said portion of the bone for abutment therewith, the prosthesis being mountable to said patient-specific augment; providing a patient-specific milling guide, the patient-specific milling guide having cutting guide surfaces which are customized in position and orientation for the particular patient and configured to guide a milling tool to form said patient-specific augment; and intra-operatively using the patient-specific milling guide to form said patient-specific augment.

DETAILED DESCRIPTION

The present disclosure describes a system and method for preparing a patient-specific artificial augment or augment for receiving a prosthetic implant in an orthopedic surgery procedure, such as but not limited to a shoulder surgery, which includes the intra-operative creation of the patient-specific augment/augment for receiving a prosthetic implant using a patient-specific surgical cutting guide.

The orthopedic surgical procedures for which the presently described system and method may be used can include, but is not limited to, the preparation of an augment or augment used in orthopedic surgery, such as a total shoulder replacement surgery (shoulder arthroplasty), total knee replacement (TKR), high tibial osteotomy (HTO), skull, or other orthopedic bone surgeries for example.

In all cases, the surgical guide as described herein is customized for an individual, or specific, patient and is thus said to be a "patient-specific" instrument or "PSI". The presently described patient-specific surgical guide permits the selected orthopedic surgical procedure to be performed in a rapid and accurate manner, and to intra-operatively create an augment or augment which is patient-specific and which thereby enables an implant (generic or patient-specific) to be mounted to the existing patient anatomy.

Augments as known and used to date in orthopedic surgery are generally non-organic and typically made of a metal, and are produced in a fixed number of different standard sizes such that a surgeon may select an appropriate size of augment during surgery from a plurality of differently sized augments produced and provided in advance of the surgery. These existing augments however cannot be modified in size or shape.

The term "augment" as used in the context of the present disclosure, however, is understood to include any element which is patient-specific, i.e. is prepared specifically for a unique individual patient, and which is configured to be disposed between the patient's bone and the prosthetic implant, such as to improve the fit or installation of the prosthetic implant and to best accommodate the anatomical structure of the patient. Such a patient-specific "augment", as described herein, may be composed of either an non-organic material or an organic material such as bone (ex: a bone graft). Possible non-organic materials for the present patient-specific augment may include, for example, Trabecular Metal™, plastic, polymer, or a biocompatible material which may be chosen to replicate bone. In all cases, however the augment described herein is able to be intra-operatively formed, such as by cutting, milling, drilling or otherwise machining, from a preliminary un-formed shape into a finished patient-specific augment shape. Accordingly, while the terms augment and metal augment may be used as specific exemplarity embodiments herein, it is to be understood that the general term "augment" as used herein is intended to be generic to both of the above-mentioned options and thus to include either a machinable non-organic material or a bone graft.

In at least one embodiment the PSI surgical guide 30 as described herein, depicted in FIGS. 4-8 for example, may be used without a navigation system, thereby permitting the reduction of overall costs for the procedure. However, in an alternate embodiment, the present PSI surgical guide 30 may also be used in conjunction with a computer assisted surgery (CAS) guidance system, whereby at least one trackable element, such as an electronic micro-electromechanical sensor (MEMS) (which may include accelerometers and/or gyroscopes for example) or alternate tracker type is affixed to at least a portion of the PSI guide 30. The trackable elements are disposed in communication with the CAS system with which they are employed such that the CAS system is then able to locate and track (i.e. navigate) the PSI guide 30 to which the trackable element is fastened.

The PSI surgical guide 30 will be described with respect to an embodiment thereof which is particularly intended for use in forming a patient-specific augment, such as a augment, which is used accommodate the mounting of an implant to the patient's existing anatomy. Such an augment, or bone graft may be used in the context of a shoulder glenoid surgery, total shoulder replacement, TKR, HTO or another orthopedic bone surgery.

However, as noted above, the PSI surgical guide itself, the system with which it is used, its method of use and the method of producing same, may also be useful for use in other orthopedic applications. Additionally, while the present PSI surgical guide will be generally described with respect to an embodiment wherein it is used to mill a augment, it may alternately be used for the formation of an artificial augment, used in place of a augment, to which the prosthetic implant is mounted.

Figure 1:
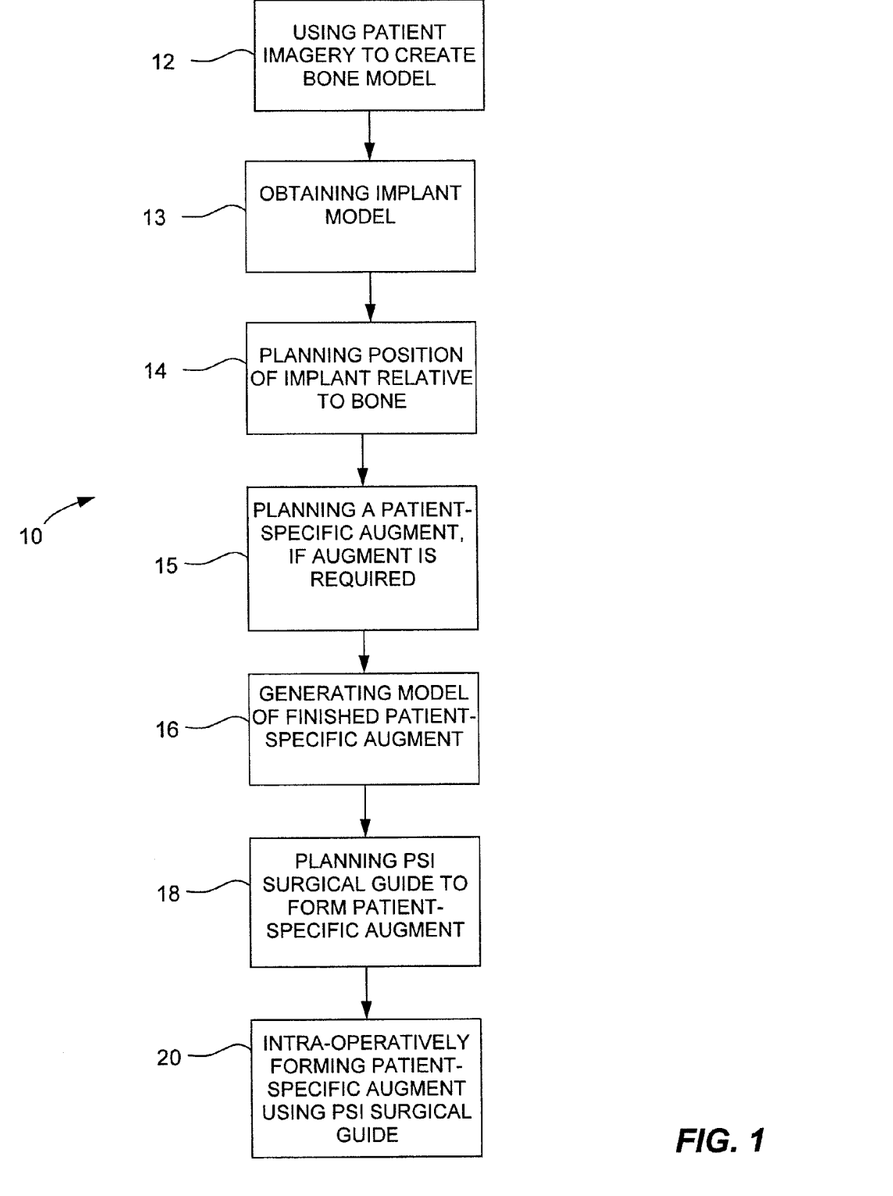
FIG. 1 is a block diagram of a method of intra-operatively forming a PSI implant augment in accordance with an embodiment of the present disclosure.
Figure 2:
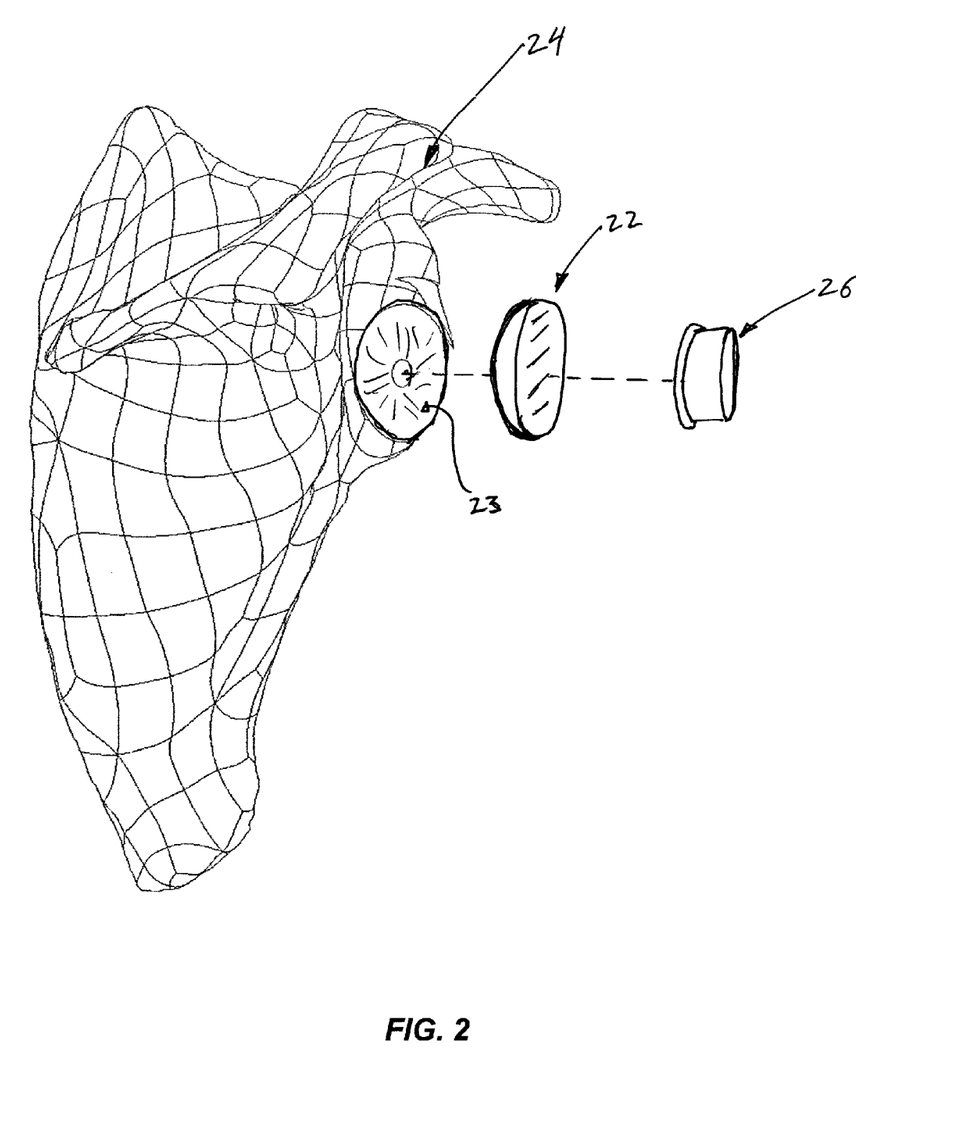
FIG. 2 is an exploded perspective view of a scapula having a PSI implant augment produced using a PSI surgical guide of the present disclosure.

Referring to FIGS. 1 and 2, an exemplary method 10 is provided for producing a patient-specific augment 22 for use in an orthopedic surgery procedure on a bone of a patient, such as an augment designed to fit within a glenoid vault 23 of a scapula 24 in a shoulder replacement surgery for example. In this particular embodiment, the patient-specific augment 22 may be a bone-graft, however as indicated above the augment 22 may alternately be made of another machinable material, such as Trabecular Metal™ for example. The patient-specific augment 22 enables a prosthetic implant 26 to be mounted to the bone 24, using the patient-specific augment 22, with the patient-specific augment 22 being disposed between the implant 26 and the bone 24. In this manner, the particular morphology of the patient's bone 24 can be accommodated by the tailor made augment 22, which abuts with and confirms to the surface of the bone, thereby allowing the implant 26 to be mounted to the bone with a precise and personalized fit and in a desired position and orientation regardless of the particular anatomical particularities of the patient's bone, which are accommodated by the augment 22. The implant 26 may therefore be either a generic implant or a patient-specific implant.

As seen in FIG. 1, the exemplary method 10 comprises first, in step 12, using patient imagery of at least a portion of the bone which is to receive the desired prosthetic implant to create a three-dimensional (3D) bone model of at least this portion of the patient's bone, if not the entire bone in question. This may include actually obtaining the patient imagery, such as recalling this imagery from a database in which it is stored following an appropriate scan (CT, or otherwise). This method 10 may be part of a larger process of virtually planning the entire orthopedic surgery to be performed using, for example, a planning software which may form part of a computer assisted surgery (CAS) system or patient-specific system for preparing and performing the given orthopedic surgery. The imaging data of the bone may be processed by a computer planning system which includes suitable computer software to generate a three-dimensional computer model of bone in question. For example, the computer planning system may include image processing software that is able to segment, or differentiate, the desired anatomic structure (e.g., bone tissue) from undesired structures (e.g., the surrounding soft tissue in the joint). Then, the image processing software generates a computer model of the desired structure. One suitable method for generating a computer model of a desired anatomic structure involves assigning a grey value to each pixel of the imaging data, setting a threshold grey value, and segmenting desired pixels from undesired pixels based on the threshold grey value.

The CAS or planning system is then used, at step 13, to obtain a 3D model, i.e. an implant model, of the desired prosthetic implant which is to be installed. This may include, for example, selecting the most appropriate implant amount a database of possible implants, which may vary in type, material, size, shape, etc. This step may further comprise selecting a model of the desired prosthesis, which may include using the computer planning system to display the computer model to the surgeon so that the surgeon can evaluate the anatomy of the joint to determine the implant solution that is optimized for the anatomical needs of the patient. Selecting the model of the desired prosthesis may involve designing a custom, patient-specific prosthesis or choosing a standard prosthesis from a set of known orthopedic prostheses. The surgeon or computer planning system may design a model of a patient-specific implant that best matches the anatomical needs of the patient. Alternatively, the planning system may access a digital database or library of known orthopedic prostheses and select a model of a desired prosthesis from the database based on the criteria established by the user.

The step 14 of planning a preferred position and orientation of the selected prosthetic implant relative to the patient's bone is then carried out, by using the implant model and the bone model to virtually adjust relative fit and positioning until the surgeon or operator is satisfied with the final position of the implant.

The system is then used, at step 15, to determine whether an augment is required to mount the prosthetic implant in the preferred position and orientation relative to the patient's bone, as determined in step 14. If an augment is in fact required, a patient-specific augment is accordingly planned such as to accommodate the anatomical characteristics and requirements of the particular patient's bone, and the selected prosthesis. Thus, the bone model obtained from patient imagery in step 12 and the implant model obtained in step 13 are used to determine a size and shape of the required patient-specific augment 22 which will correspond to the surface of the bone with which the augment is to be abutted and thus to which the implant is to be mounted.

At step 16, the method then includes generating or otherwise creating a virtual, three-dimensional (3D) model of the finished patient-specific augment 22, which has the planned size and shape determined in step 15. This is accomplished by the planning software/system, and may include displaying a visual representation of the 3D model of the finished patient-specific augment, and overlaying same with the patient imagery of the bone. This step may include using the computer models of the patient's bone, the plane patient-specific augment, and the selected prosthesis, to determine the desired size and relative position and orientation of each. According to an exemplary embodiment of the present disclosure, the surgeon overlays a digital representation or image of the desired prosthesis and planned patient-specific augment onto the computer model of the bone, to ensure the proper size of the desired prosthesis and augment.

This enables the system to then plan and create, at step 18, a patient-specific surgical guide (such as a cutting and/or milling guide 30 as will be described in further detail below), which has cutting guide surfaces thereon which are customized in position and orientation and configured to guide a surgical implement to form the patient-specific augment 22 corresponding to planned virtual 3D model of step 16. Accordingly, a patient-specific surgical guide 30 is provided, using the results of steps 12-16, which has cutting guide surfaces thereon that are customized in position and orientation for the specific and configured to guide a surgical implement, such as a milling tool, to form the patient-specific augment 22 from the original, unformed, augment blank.

This step may thus comprise using the computer planning system to design a custom, patient-specific surgical guide 30 (as will be described in further detail below—see FIG. 4) based on the method steps 12-16 described above. For example, the computer planning system may determine the shape and size of platform 32 and/or the guide slots or milling tracks 50 in the cutting guide 34. The patient-specific guide 30 may be an entirely custom product that is manufactured using a casting/molding process or a rapid prototyping process, such as 3-D printing, stereolithography, selective laser sintering, fused deposition modeling, laminated object manufacturing, or electron beam melting, for example. Alternately, the patient-specific guide 30 may be manufactured by removing material from a standard guide (e.g. by forming the guide slots 50 in the cutting guide 34 in a manner specific to the particular patient. With the guide 30 will generally be described below as having a base fixture 32 and a patient-specific cutting guide 34, it is to be understood that the base fixture may also be patient-specific, or it may alternately be standardized.

Then, at step 20, the patient-specific augment 22 is intra-operatively created, using the patient-specific surgical guide 30, to form the final patient-specific augment 22 which corresponds to the planned virtual 3D model by milling, cutting, or otherwise machining the augment into the patient-specific augment 22 having the size and shape corresponding to the planned virtual 3D model.

In one particular embodiment, as shown in FIG. 2 for example, the bone is a scapula 24 and the prosthetic implant 26 is a glenoid implant. The step of planning the patient-specific augment may therefore further include forming the planned patient-specific augment 22 to conform with the glenoid vault 23 of the scapula.

In a further particular embodiment, the patient-specific surgical guide is a milling guide 30, as will be described, and therefore the step 20 of intra-operatively creating the patient-specific augment may further comprise milling the unformed augment blank using a milling tool guided by the cutting guide surfaces of the patient-specific surgical guide.

As noted above, in one possible embodiment the surgical guide as described herein may alternately be used in conjunction with a CAS guidance system. In this embodiment, therefore, the method may further comprise providing the patient-specific surgical guide with at least one trackable element thereon, the trackable element being operable for communication with the CAS guidance system.

In a further embodiment of the method 10 for preparing a patient-specific augment use in an orthopedic procedure, the method may comprises the steps of: a) providing a digital model of the bone; b) identifying a portion of the bone adapted to receive the prosthesis and determining a preferred position and orientation of the prosthesis relative to the portion of the bone; c) determining a size and shape of a patient-specific augment having at least one bone-engaging surface corresponding to the portion of the bone, such that the patient-specific augment conforms to the portion of the bone for abutment therewith, the prosthesis being mountable to the patient-specific augment; d) providing a patient-specific milling guide, the patient-specific milling guide having cutting guide surfaces which are customized in position and orientation for the particular patient and configured to guide a milling tool to form the patient-specific augment; and e) intra-operatively using the patient-specific milling guide to form the patient-specific augment.

The method described above may also include inlaying the patient-specific augment on the portion of the bone by positioning a bone-engaging surface of the patient-specific augment against a surface of the portion of the bone, and mounting the prosthesis onto the patient-specific augment.

The method described above may also include the step of providing a digital model of the patient-specific augment, and overlaying the digital model of the patient-specific augment onto the digital model of the bone.

The step e) described above may, in one particular embodiment, further include intra-operatively milling an un-formed augment into the patient-specific augment. The method may also further include planning and creating the patient-specific milling guide intra-operatively, based on the determined size and shape of the patient-specific augment.

Figure 3:
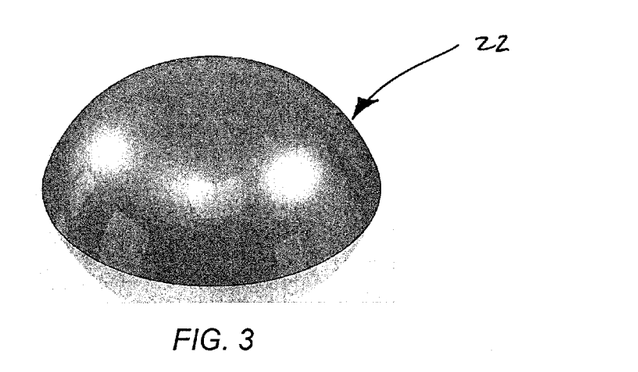
FIG. 3 is a perspective view of a patient-specific augment in accordance with one particular exemplary embodiment.

FIG. 3 depicts a model of a finished patient-specific augment 22 produce in accordance with the above-mentioned method and using the patient-specific surgical guide 30 as will be described in further detail below. In this particular exemplary embodiment, the finished patient-specific augment 22 has a substantially hemi-spherical shape. However, it is to be understood that the patient-specific augment 22 may have any required shape, in order to accommodate both the particular anatomical features of the particular patient's bone surface and the prosthetic implant which is to be installed on the bone. The shape of the patient-specific augment 22 will reflect the corresponding shape of the cutting guide portion 34 of the surgical guide 30, which is used to form the patient-specific augment 22 as will be seen below. As such, the cutting guide 34 of the surgical guide 30 is itself tailor made, i.e. patient-specific, such as to produce the desired shape of the required patient-specific augment 22.

Figure 7A:
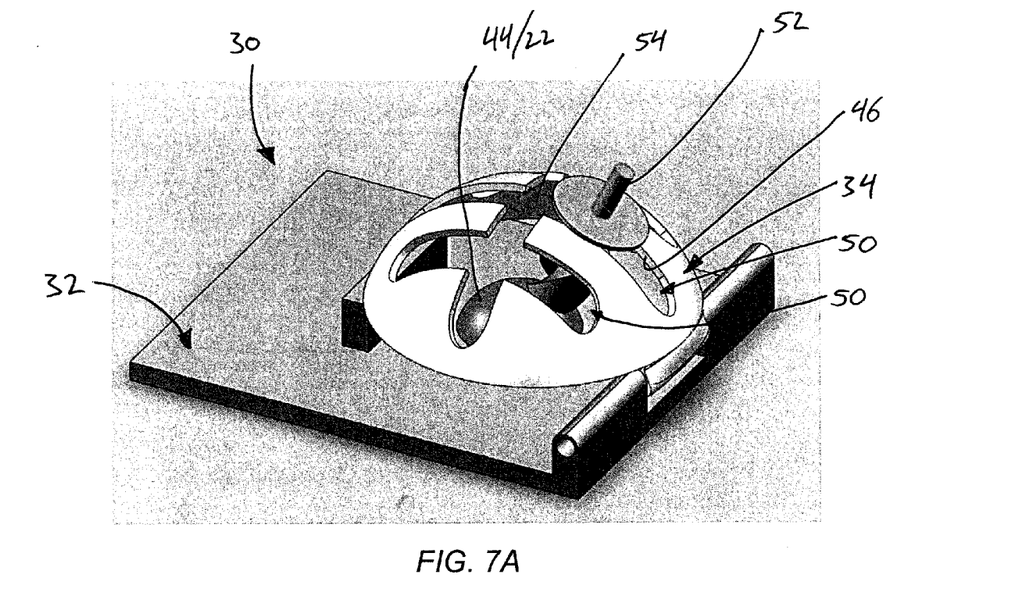
FIG. 7A is a perspective view of the PSI surgical guide of FIG. 6, showing a bone milling tool machining the augment blank using the PSI cutting guide.
Figure 7B:
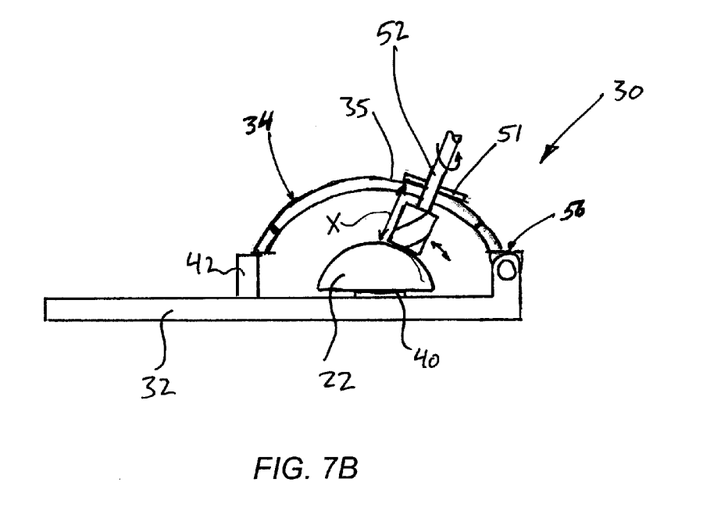
FIG. 7B is a cross-sectional view of the PSI surgical guide as shown in FIG. 7A, showing the bone milling tool machining the unformed augment using the PSI cutting guide.

As best seen in FIG. 7B for example, by providing the cutting guide 34 of the patient-specific surgical guide 30 with a particular shape, the patient-specific augment 22 formed using the cutting guide 34 will have a corresponding shape, given that the cutting tool 52 (in the depicted embodiment a milling tool) uses the surfaces of the cutting guide 34 as a guide. It is therefore to be understood that the patient-specific cutting guide 34 of the surgical guide 30 may have any suitable shape and form, which is selected and dictated such as to produce the desired shape and form of the patient-specific augment 22. As seen in FIG. 7B, the patient-specific augment 22 created by the PSI cutting guide 34 has an outer surface that is offset by a distance "X" from the outer surface 35 of the overlying cutting guide 34, but otherwise shares the same shape, because the milling tool 52 has a guide 51 which is abutted against the outer surface 35 as it moves along the PSI cutting guide 34. While a milling guide 34 is depicted, such an "offset" would also be present if another type of cutting guide is used, such as a saw guide, drill guide, etc.

The patient-specific augment 22 may also itself serve as an implant in certain circumstances, in which case an additional prosthetic implant may not be required. For example, the patient-specific augment 22 may be a bone graft which is so formed to avoid the need for an implant (ex: by reconstructing the glenoid vault, while forming the joint with an existing proximal humerus for example). A patient-specific version of the bone graft glenoid implant as described in International patent application no. PCT/CA2013/050253 filed Mar. 28, 2013 is also possible. The entire contents of International patent application no. PCT/CA2013/050253 is incorporated herein by reference. Alternately, the patient-specific augment 22 may be formed of a trabecular metal TM, an thus may have a patient-specific bone-abutting portion and an implant like opposed portion, which are integrally formed as a single unity augment 22.

Referring now to FIGS. 4-8, the patient-specific surgical guide 30 will now be described in further detail. The patient-specific surgical guide 30, which may be a milling guide for example, is used for the intra-operative creation of a patient-specific augment 22 (or, alternately, a formable inorganic augment) which is adapted for use in mounting a prosthetic implant on a bone of a patient. In the depicted embodiment, the surgical guide 30 is a milling guide used for the creation of a augment adapted to fit within a glenoid vault 23 of a patient's scapula 24 (see FIG. 2), however other applications remain possible.

Figure 6:
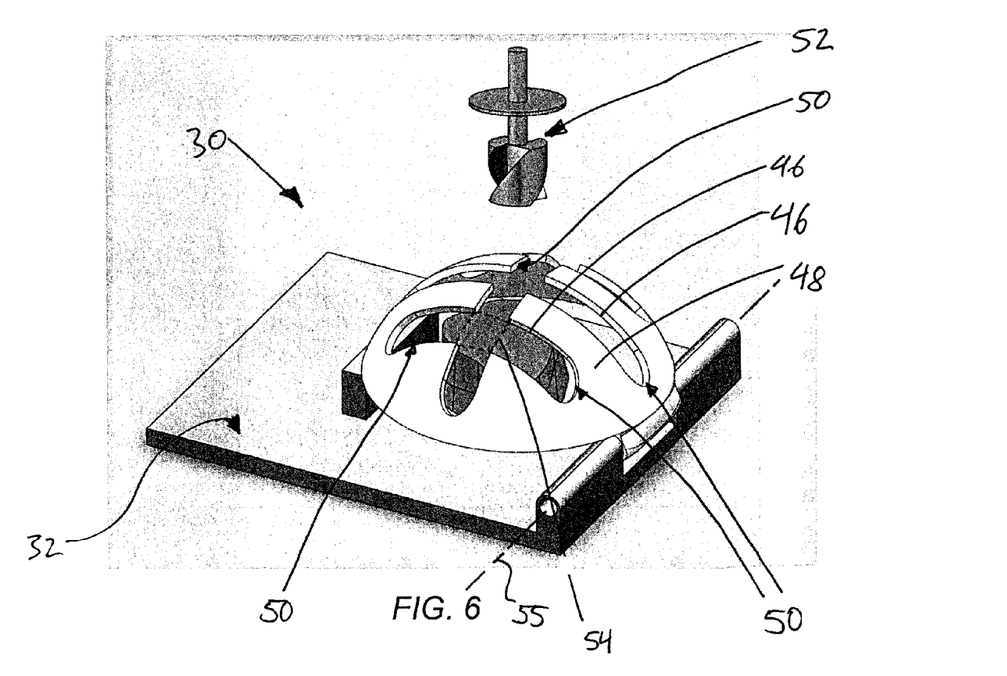
FIG. 6 is a perspective view of the PSI surgical guide of FIG. 5, shown with a PSI cutting guide element thereof in an operative position for milling the un-formed augment blank.

The patient-specific surgical guide 30 includes generally a base fixture or platform 32 to which is engaged a patient-specific cutting guide 34. The base fixture 32 may comprise a flat platform, and includes a mounting surface 36 on an upper side thereof. The upper mounting surface 36 defines thereon a bone retaining portion 38. In the depicted embodiment, this bone retaining portion 38 includes a protruding pedestal 40 upon which the augment is received and mounted. The pedestal 40 of the bone retaining portion 38 is positioned on the base fixture 32 in a location which is centrally positioned within the patient-specific cutting guide, when it is disposed in the closed (operable) position thereof as shown in FIG. 6. The bone retaining portion 38 may include a fastener (not shown), such as a spike, pin, clamp, screw thread, or the like, which helps retain the augment in position on the pedestal 40. The base fixture 32 may also include a guide stop 42 which protrudes from the upper mounting surface 36 and against which the patient-specific cutting guide 34 rests when in the closed position, as will be described in further detail below. The pedestal 40 of the bone retaining portion 38 is therefore located between the guide stop 42 and one end 43 of the base fixture 32 with which the patient-specific cutting guide 34 is engaged.

Figure 4:
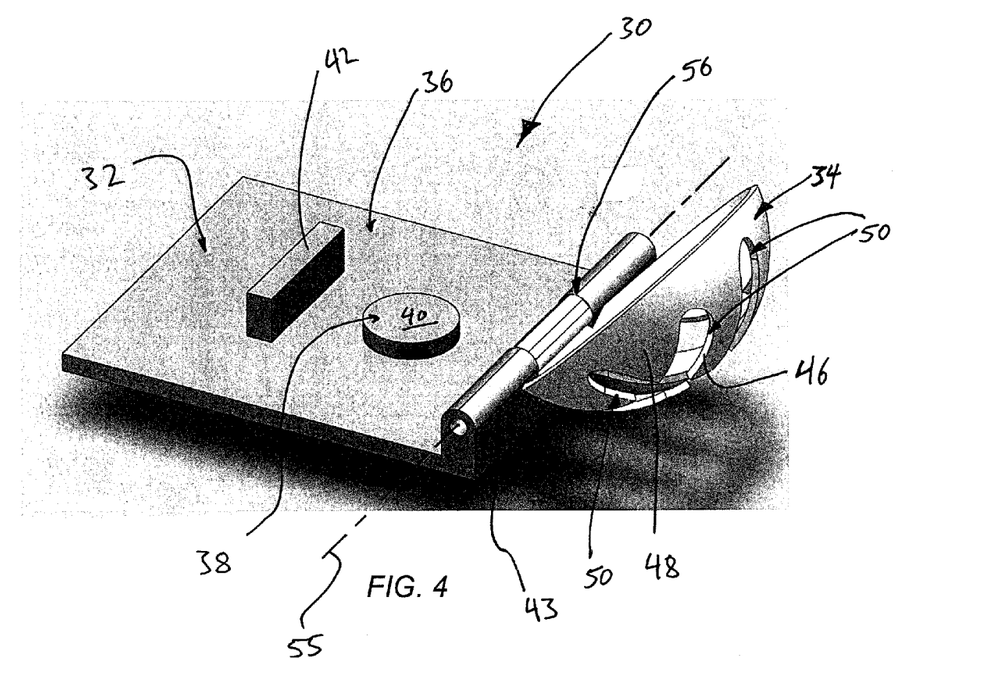
FIG. 4 is a perspective view of a PSI surgical guide for forming the patient-specific augment.
Figure 5:
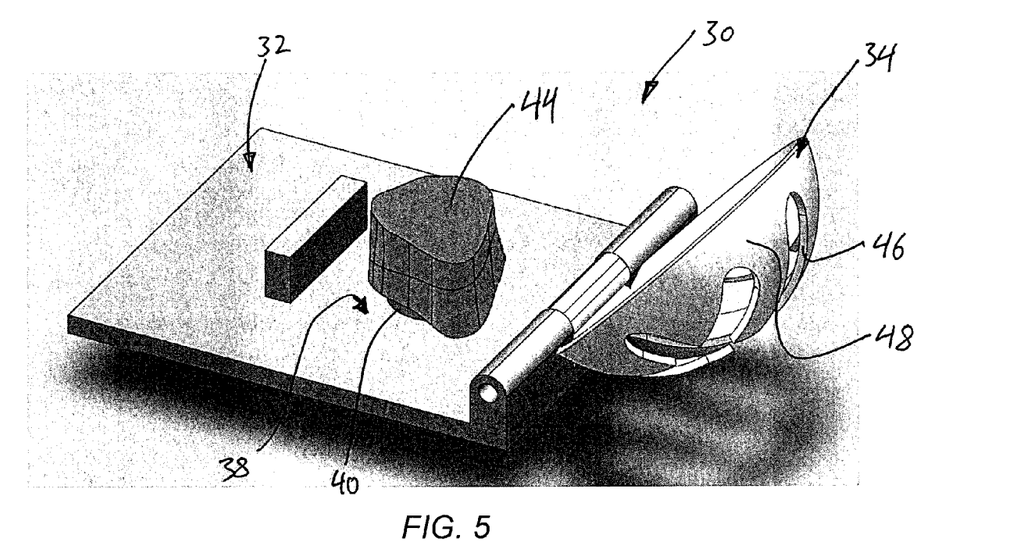
FIG. 5 is a perspective view of the PSI surgical guide of FIG. 4, shown with an un-formed augment blank in place therewithin, which is to be used to form the patient-specific augment.

Referring now to FIGS. 4-6, the patient-specific cutting guide 34 includes one or more cutting guide surfaces 46 defined thereon which are customized in position and orientation on the patient-specific cutting guide 34 for the particular patient undergoing surgery. These cutting guide surfaces 46 of the patient-specific cutting guide 34 are therefore selected and uniquely configured in position, orientation, size, etc., to guide a chosen surgical implement to re-shape the unformed augment blank 44 into the final patient-specific augment 22 desired.

While several different embodiments of the patient-specific cutting guide 34 are possible, in at least the depicted embodiment the cutting guide 34 includes a semi-spherical shaped shell 48 having one or more guide slots 50 formed therein. The guide slot 50 have lateral edges thereof which form the cutting guide surfaces 46, and are configured to receiving a surgical implement, such as a milling burr 52, therethrough. These guide slots 50 accordingly form milling tracks, along which a milling tool 52 or other cutting implement can be displaced. In the particular embodiment depicted, the patient-specific cutting guide 34 comprises a plurality of guide slots 50 which are arranged in a selected pattern such as to permit the milling tool 52 to move along at least two different axes. In one embodiment, the plurality of guide slots 50 includes at least a first guide slot extending in a first direction and at least a second guides slot extending in a second direction substantially perpendicular to the first direction, whereby the axes of each of the transverse guide slots 50 are substantially perpendicular to each other. These first and second guide slots 50 intersect each other at openings 54, which are sufficiently large to permit the milling tool 52 to pass therethrough.

As seen in FIG. 4-6, the patient-specific cutting guide 34 is mounted to the base fixture 32 for displacement between an open, inoperable, position as shown in FIG. 4, and a closed, bone cutting, position as shown in FIG. 6. In the open inoperable position, the bone retaining portion 38 of the base fixture 32 is open an accessible, thereby permitting an unformed augment blank 44 or other bone structure to be positioned therewithin on the pedestal 40, as shown in FIG. 5. Once the unformed augment blank 44 is in position within the bone retaining portion 38 of the base fixture 32, and fastened in place thereon if necessary, the patient-specific cutting guide 34 is then displaced from its open inoperable position into its closed bone cutting position, as shown in FIG. 6. In this closed bone cutting position, the cutting guide surfaces 46 of the of the patient-specific cutting guide 34 are disposed in position to allow the re-shaping of the unformed augment blank 44 into the finished patient-specific augment 22.

The patient-specific cutting guide 34 may be pivotally mounted to the base fixture 32 by a hinge 56, for pivoting movement between the open (FIG. 4) and closed (FIG. 6) positions thereof about an axis of rotation 55 which is defined by the hinge 56 and extends substantially transverse to the base fixture 32 at the end 43 thereof. The cutting guide 34 may be alternately mounted to the base fixture 32 for displacement between the open and closed positions, for example by a sliding mechanism or a vertical pivot join, in order to enable sliding translation or rotation about a vertical axis of rotation respectively. The patient-specific cutting guide 34 may be removably engaged to the base fixture 32, such as to be attached to and removed therefrom as required. In this manner, the base fixture 32 may be generic, and only the cutting guide 34 need be created or modified such as to be patient-specific. As such, the cutting guide 34 may be interchangeable, such that the same base fixture 32 can be used with different selected patient-specific cutting guides 34.

Figure 8:
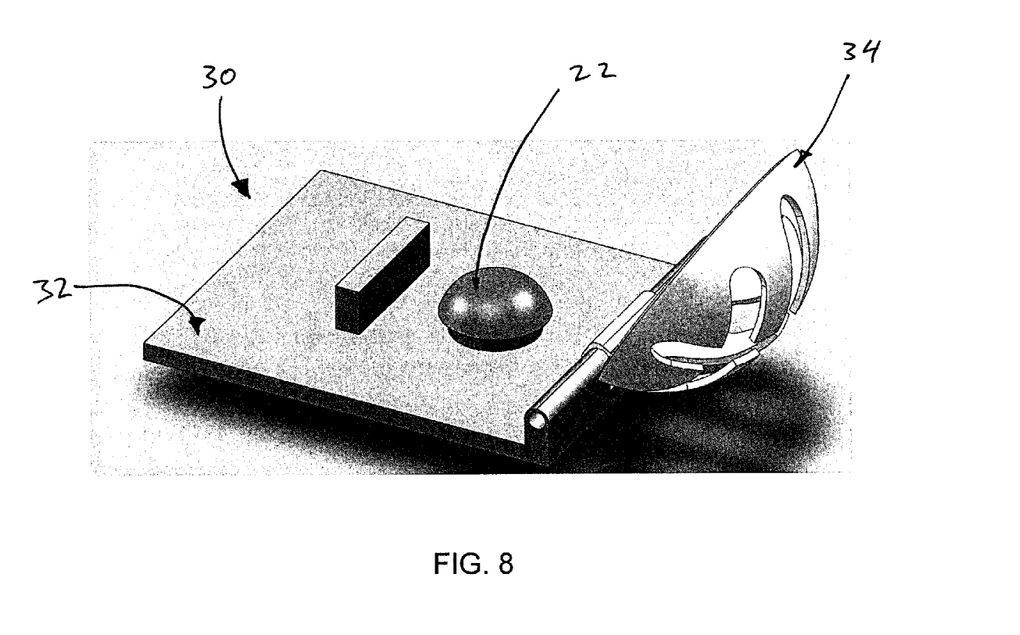
FIG. 8 is a perspective view of the PSI surgical guide of FIG. 4, shown with the PSI cutting guide element in an open position and the finished patient-specific augment.

As seen in FIGS. 7-8, once the patient-specific cutting guide 34 is moved into its closed bone cutting position (FIG. 7), it lies overtop of the unformed augment blank 44 position within the bone receiving portion 38 of the device. The surgical cutting implement, which in this embodiment is a milling tool 52, is inserted through the opening(s) 54 in the cutting guide 34 and displaced by a suitable milling machine, using the cutting guide surfaces 46 of the slots 50 in the patient-specific cutting guide 34, in order to machine the bone such as to form the finished patient-specific augment 22 (FIG. 8) which has a size and shape corresponding to the planned 3D model thereof. Once so formed, the finished patient-specific augment 22 is removed from the surgical guide 30 and is then ready to be used in the surgical procedure. In the case of the afore-mentioned shoulder surgery, for example, the patient-specific augment 22 is formed such as to be received within the patient's glenoid vault 22, in order to permit the abutment of a prosthetic glenoid implant 26 against the augment 22 (see FIG. 2).

This process of machining the unformed augment blank 44 into the finished/planned patient-specific augment 22, as shown in FIGS. 7-8, is accordingly performed intra-operatively using the present surgical guide 30, of which at least the cutting guide portion 34 thereof is patient-specific and thus created purposely form the particular patient undergoing the orthopedic surgical procedure based on their anatomical features and the required prosthetic implant.

The presently described patient-specific surgical guide 30 may form part of a larger orthopedic system, provided for preparing a patient's bone to receive a given prosthetic implant, for example. This system may include the patient-specific surgical guide 30, the milling tool 52 or other surgical cutting/machining implement and the milling or other machine operating such a tool, and an associated CAS computer running a planning software for at least planning the desired patient-specific augment and the patient-specific guide for creation of same, and, optionally, for performing the given orthopedic surgery.

The patient-specific surgical guide 30 as described herein may be constructed of a material that is able to withstand contact from the milling tool 52 and/or other cutting tool or surgical implement. In certain embodiments, at least the patient-specific cutting guide 34 may be constructed entirely of a suitable plastic or metal. In other embodiments, guide assembly 30 may be constructed of more than one material. For example, at least the cutting guide 34 may be constructed of metal to withstand contact from milling tool 52, while the base fixture 32 may be constructed of plastic. Alternately, the cutting guide 34, if it is intended only to contact a shaft of the cutting tool 52 free of cutting edges, the cutting guide 34 may be made of plastic while the base 32 may be made of metal or other suitable more durable material in the event that the cutting edges of the milling tool 52 contact the base fixture 32 during machining of the augment.

The base fixtures 32 may therefore be standard, ready-made components, and the custom-made patient-specific cutting guide 34, once created, may be snapped or otherwise fastened in place to the generic base 32. Accordingly, in this embodiment the guide assembly 30 preferably permits intra-operative customization. For example, a set of modular platforms 32 may be provided, and the surgeon may choose, intra-operatively, the desired platform 32 to be used with the patient-specific cutting guide 34, once created.

The above description is meant to be exemplary only, and one skilled in the art will recognize that changes may be made to the embodiments described. Still other modifications which fall within the scope of the present invention will be apparent to those skilled in the art, in light of a review of this disclosure, and such modifications are intended to fall within the appended claims.

The invention claimed is:

1. A patient-specific surgical guide for intra-operatively creating a patient-specific augment adapted for mounting a prosthetic implant on a bone of a patient, the patient-specific surgical guide comprising:
   a base fixture including a mounting surface having a bone retaining portion thereon within which an unformed augment blank is receivable; and
   an interchangeable patient-specific cutting guide removably engaged to the base fixture, the patient-specific cutting guide including a semi-spherical shaped shell having one or more guide slots formed therein, the guide slots defining cutting guide surfaces which are customized in position and orientation for said patient and configured to guide a surgical implement to re-shape the unformed augment blank to create said patient-specific augment, wherein the patient-specific augment has a size and shape corresponding to a portion of the bone adapted to receive the prosthetic implant such that the patient-specific augment will conform to said portion of the bone for abutment therewith;
   wherein the patient-specific cutting guide is mounted to the base fixture for displacement between an open inoperable position and a closed bone cutting position, the bone retaining portion of the base fixture being accessible to receive the unformed augment blank therein when the patient-specific cutting guide is disposed in the open inoperable position, and the cutting guide surfaces of the patient-specific cutting guide being disposed in position to allow said re-shaping of the unformed augment blank when the patient-specific cutting guide is disposed in said closed bone cutting position.

2. The patient-specific surgical guide of claim 1, wherein the guide slots in the semi-spherical shaped shell include at least a first guide slot extending in a first direction and at least a second guide slot extending in a second direction substantially perpendicular to the first direction, the first and second guide slots intersecting each other.

3. The patient-specific surgical guide of claim 1, wherein the patient-specific cutting guide is engaged to the base fixture by a hinge, the patient-specific cutting guide being pivotable between the open inoperable position and the closed bone cutting position about an axis of rotation defined by the hinge.

4. The patient-specific surgical guide of claim 1, wherein the surgical implement is a milling tool, the patient-specific cutting guide being a milling guide and the one or more cutting guide surfaces thereof comprising guide slots disposed through the milling guide and sized to receive at least a portion of a bone milling burr therethrough.

5. The patient-specific surgical guide of claim 1, further comprising at least one trackable element fixed to a portion thereof, the trackable element being operable for communication with a computer assisted surgery guidance system.

6. The patient-specific surgical guide of claim 5, wherein the trackable element includes an electronic micro-electro-mechanical sensor (MEMS) operable to determine and provide at least orientation data of said portion of the patient-specific surgical guide to the computer assisted surgery guidance system.

7. The patient-specific surgical guide of claim 1, wherein the unformed augment blank is one of a non-organic material or a bone graft.

8. An orthopedic guide for intra-operatively preparing a particular patient's bone to receive a prosthesis, the orthopedic guide comprising:
   a base fixture including a mounting surface having a bone retaining portion thereon within which an unformed augment blank is receivable; and
   an interchangeable patient-specific cutting guide removably engaged to the base fixture and mounted thereto for displacement between an open inoperable position and a closed bone cutting position, the patient-specific cutting guide including a semi-spherical shaped shell having one or more guide slots formed therein, the guide slots defining cutting guide surfaces which are customized in position and orientation for said patient, the cutting guide surfaces being configured to guide a cutting tool therethrough to re-shape the unformed augment blank on the base fixture into a patient-specific augment, the patient-specific augment including at least one surface thereon having a size and shape corresponding to the particular patient's bone and adapted to fit against the particular patient's bone, such that the patient-specific augment is mountable between the particular patient's bone and the prosthesis.

9. The orthopedic guide of claim 8, wherein the bone retaining portion of the base fixture is accessible to receive the unformed augment when the patient-specific cutting guide is disposed in said open inoperable position, and the cutting guide surfaces of the patient-specific cutting guide being disposed in position to allow said re-shaping of the unformed augment when the patient-specific cutting guide is disposed in said closed bone cutting position.

10. The orthopedic guide of claim 9, wherein the patient-specific cutting guide is engaged to the base fixture by a hinge, the patient-specific cutting guide being pivotable between the open inoperable position and the closed bone cutting position about an axis of rotation defined by the hinge.

11. The orthopedic guide of claim 8, wherein the patient-specific cutting guide comprises a plurality of said guide slots, said guide slots includes at least a first guide slot extending in a first direction and at least a second guide slot extending in a second direction substantially perpendicular to the first direction, the first and second guide slots intersecting each other.

12. The orthopedic guide of claim 8, wherein the orthopedic guide is a milling guide and the cutting tool is a milling tool adapted to be used with the milling guide to cut the unformed augment blank to form the patient-specific augment.

13. The orthopedic guide of claim 8, further comprising at least one trackable element fixed to a portion thereof, the trackable element being operable for communication with a computer assisted surgery guidance system.

14. The orthopedic guide of claim 13, wherein the trackable element includes an electronic micro-electromechanical sensor (MEMS) operable to determine and provide at least orientation data of said portion of the orthopedic milling guide to the computer assisted surgery guidance system.

* * * * *